United States Patent
Huo et al.

(10) Patent No.: US 8,073,229 B2
(45) Date of Patent: Dec. 6, 2011

(54) IMAGE ANALYSIS OF TUBE TIP POSITIONING

(75) Inventors: Zhimin Huo, Pittsford, NY (US); Jing Zhang, Shanghi (CN); Minjie Chen, Shanghi (CN)

(73) Assignee: Carestream Health, Inc., Rochester, NY (US)

( * ) Notice: Subject to any disclaimer, the term of this patent is extended or adjusted under 35 U.S.C. 154(b) by 1021 days.

(21) Appl. No.: 11/942,021

(22) Filed: Nov. 19, 2007

(65) Prior Publication Data

US 2009/0129654 A1 May 21, 2009

(51) Int. Cl.
*G06K 9/00* (2006.01)
(52) U.S. Cl. ...................................................... 382/132
(58) Field of Classification Search .................. 382/128, 382/132
See application file for complete search history.

(56) References Cited

U.S. PATENT DOCUMENTS

| | | | | |
|---|---|---|---|---|
| 5,859,922 | A * | 1/1999 | Hoffmann | 382/128 |
| 7,840,055 | B2 * | 11/2010 | Huo | 382/132 |
| 2008/0015590 | A1 * | 1/2008 | Sanders et al. | 606/69 |
| 2008/0039715 | A1 * | 2/2008 | Wilson et al. | 600/424 |

OTHER PUBLICATIONS

Commonly assigned U.S. Appl. No. 60/880,300, titled: Computer-Aided Tube and Tip Detection, Huo et al., filed Nov. 21, 2006.
Commonly assigned U.S. Appl. No. 11/644,858, titled: Computer-Aided Tube and Tip Detection, Huo et al., filed Dec. 22, 2006.

* cited by examiner

*Primary Examiner* — Andrew W Johns

(57) ABSTRACT

A method for processing a radiographic image of a patient obtains radiographic image data and detects the position of inserted tubing or other foreign object in the obtained image and determines the tubing tip or object location. A region of interest in the neighborhood of the tubing tip or object location is defined and at least one anatomy structure within the region of interest is detected. The probability for mal-positioning of the tip or object is calculated by determining the position of the tip or object relative to the at least one anatomy structure.

24 Claims, 23 Drawing Sheets

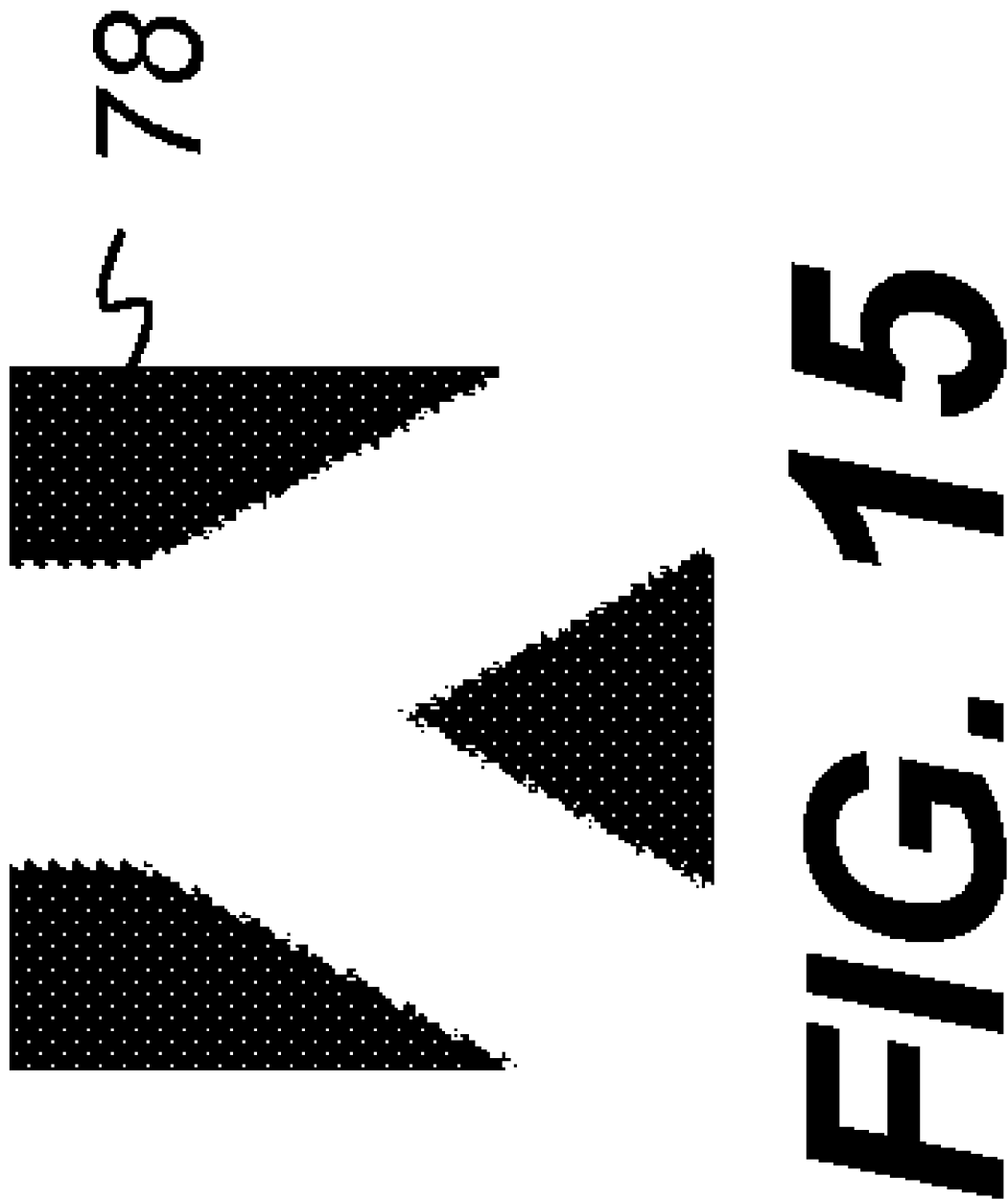

IMAGE ANALYSIS OF TUBE TIP POSITIONING

CROSS REFERENCE TO RELATED APPLICATIONS

Reference is made to commonly assigned (a) U.S. Patent Application Ser. No. 60/880,300 entitled "Computer-Aided Tube and Tip Detection" by Huo et al filed Nov. 21, 2006; and (b) U.S. patent application Ser. No. 11/644,858 entitled "Computer-Aided Tube and Tip Detection" by Huo, et al. filed Dec. 22, 2006, the disclosures of which hereby are incorporated by reference in this application.

FIELD OF THE INVENTION

This invention generally relates to processing of diagnostic images and more particularly relates to a method for enhancing diagnostic images in order to detect the tip position of a tube positioned within the patient.

BACKGROUND OF THE INVENTION

Clinical evaluation of patients in an Intensive Care Unit (ICU) often relies heavily on diagnostic images, such as portable chest radiographic images, for example. It has been noted that chest radiographs can be particularly helpful in the ICU for indicating significant or unexpected conditions requiring changes in patient management. To meet the need for readily accessible and rapid diagnostic imaging, equipment such as portable chest radiography equipment has been developed, allowing the ICU clinician to conveniently obtain a radiographic image as needed for the patient.

One concern for effective patient treatment relates to the ability to detect the proper positioning of the tip of a tube that has been inserted into the patient. Possible tube types include, for example, endo-tracheal (ET) tubes, feeding (FT) tubes, and nasogastric (NT) tubes. Proper tip positioning can help to insure delivery or disposal of liquids and gases to and from the patient during a treatment procedure. Improper tip positioning can cause patient discomfort, render a treatment ineffective, or even be life-threatening. Other types of medical devices that are inserted into the body also require proper positioning, such as pacemakers, balloon catheters and stents.

Techniques for computer-assisted tube tip detection have proved to be error-prone, making mal-positioning difficult to detect in some cases. Even though tubing, wires, and other apparatus used to support the patient appear in a radiographic image, little or no attention has been paid to using automated image analysis techniques to detect tube tip position. Image processing techniques have thus far been directed more to eliminating unwanted effects of tube and tip structure detected in the obtained image than to the task of determining the position of the tip itself. There is, then, a need for a diagnostic imaging method for detecting and identifying tube tip positioning.

SUMMARY OF THE INVENTION

An object of the present invention is to address the need for tube tip positioning detection in a radiographic image. With this object in mind, the present invention provides a method for processing a radiographic image of a patient comprising steps of: obtaining radiographic image data; detecting the position of inserted tubing or other foreign object in the obtained image and determining the tubing tip or object location; defining a region of interest in the neighborhood of the tubing tip or object location; detecting at least one anatomy structure within the region of interest; and calculating the probability for tip or object mal-positioning by determining the position of the tip or object relative to the at least one anatomy structure.

Embodiments of the present invention provide automated detection of tube tip or object positioning and calculate the probability of mal-positioning. Using methods of the present invention, it is possible to warn an operator or clinician of a mal-positioning condition and to display the relative tube tip or object position for visual confirmation of a positioning problem.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

FIGS. 14A through 14E show various stages in ROI processing following the sequence given in FIG. 12;

FIG. 15 shows a template used in carina detection in one embodiment;

DETAILED DESCRIPTION OF THE INVENTION

It is to be understood that elements not specifically shown or described in this description may take various forms well known to those skilled in the art. The description that follows focuses on tip detection for an ET tube as one example of the method of the present invention. It can be appreciated that similar steps would apply for detection of tips for other types of tubing, with the necessary adaptation for surrounding anatomy.

The ideal position of the ET tube is 3-4 cm above the carina. Flexion and extension of the patient's neck can result in migrating and mal-positioning of an ET tip. When the ET tube is mal-positioned within a mainstem bronchus, complete atelectasis of the contralateral lung is likely, accompanied by difficulties with mechanical ventilation. When the ET tube is mal-positioned within the superior trachea, there is a risk of accidental extubation and vocal cord injury. According to one study, ET tube mal-positioning occurs in approximately 15% of patients. The use of routine post-intubation chest radiography has been recommended for detection of ET tube mal-positioning for which clinical diagnosis is unreliable, since it is often difficult to identify specific pulmonary complications on the basis of clinical examination alone.

In the clinical setting, it is recognized that merely detecting the path of the tube and its tip is not sufficient for determining whether or not the tube structure is able to perform its function. For the attending medical personnel, it is important to be able to ascertain that the tip of a tube is at the right position relative to the patient's anatomy.

The method of the present invention takes this into account and provides the attending medical personnel with a probabilistic assessment of tip positioning suitability for the particular patient.

Figure 1:
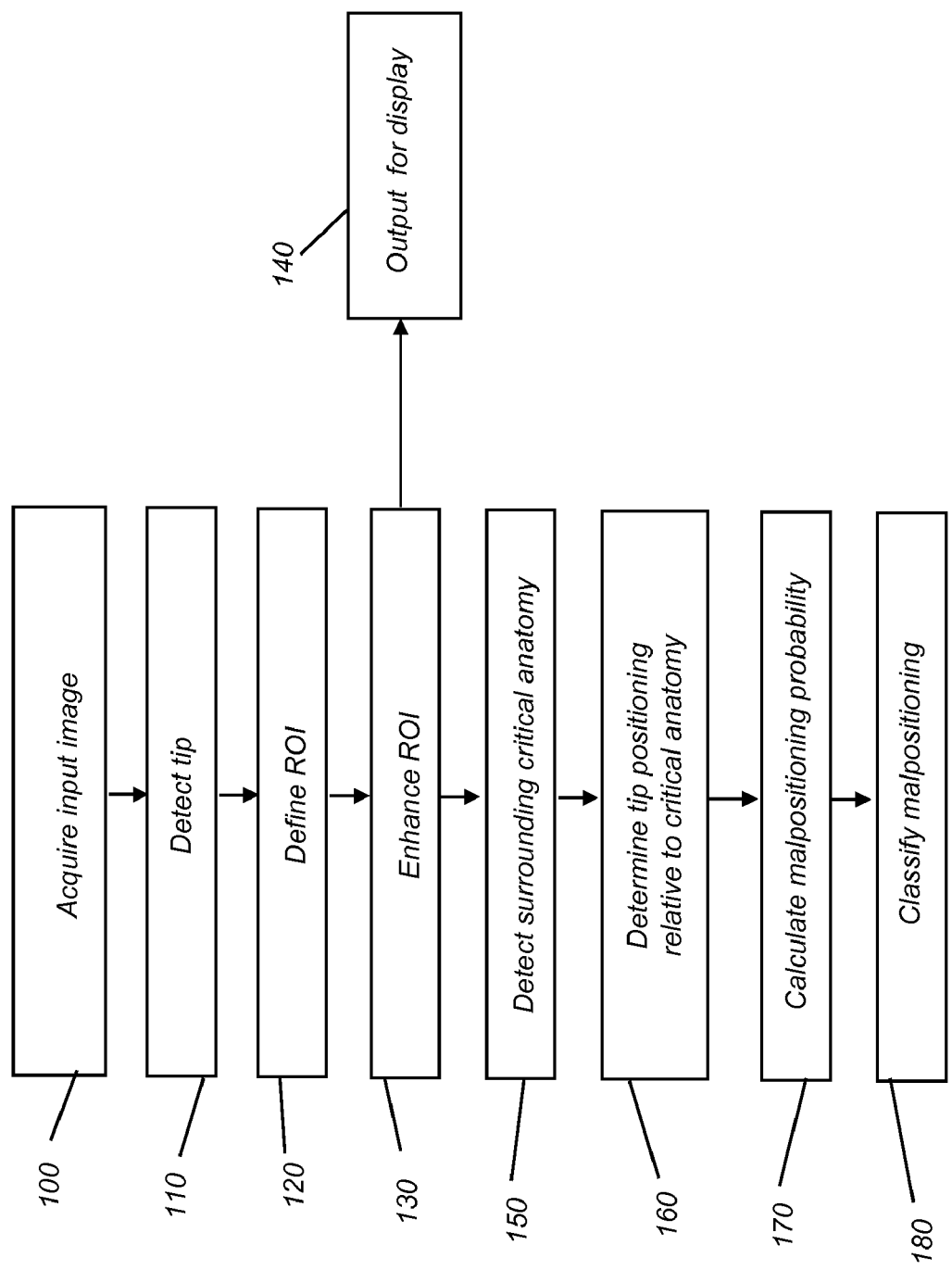
FIG. 1 is a logic flow diagram showing a basic sequence for tip detection in embodiments of the present invention.

The present invention provides a method for automated detection and reporting of tube tip position from a radiographic image. The logic flow diagram of FIG. 1 shows the overall steps that can be used for comprehensive tip detection, display, and automated assessment in one software application that runs on a computer associated with the X-ray system providing the radiographic images. An initial step 100 acquires the input radiographic image that contains the tube and tip. A tip detection step 110 is then executed in order to detect the tip. Following tip detection, a Region of Interest (ROI) is defined in an ROI definition step 120. Enhancement of the ROI follows in an ROI enhancement step 130. Following this, a display output step 140 directs the enhanced ROI image to a display monitor. Display output step 140 could also be executed following any of the subsequent processing steps shown in FIG. 1. In addition, the enhanced image is also processed further in an anatomy detection step 150. A relative positioning determination step 160 is then executed to determine the relative position of the tip and nearby critical anatomy structures. A mal-positioning probability can then be determined in a probability calculation step 170. This probability value can be provided to the attending medical personnel, either reported on the display monitor or in some other form. An optional classification step 180 then classifies possible mal-positioning of the tip according to predetermined criteria.

Tip detection step 110 can be executed using any of a number of approaches for locating the tube and its tip. One of the possible methods that can be used is disclosed in the earlier-cited commonly assigned U.S. patent application entitled "Computer-Aided Tube and Tip Detection" by Huo et al. Huo, et al. disclosed techniques such as edge enhancement, edge detection, and line segment tracing for use to differentiate tubing from anatomical structures having well-defined edges. Known utilities such as Canny edge detection and Hough transforms are used to identify tubing structures within a defined ROI. Other known techniques can similarly be used to provide tube and tip detection. One advantage of the method described by Huo et al relates to detecting the type of tube according to factors such as width and placement. For the methods of the present invention the type and physical characteristics of the tube to be identified must be known.

Figure 2:
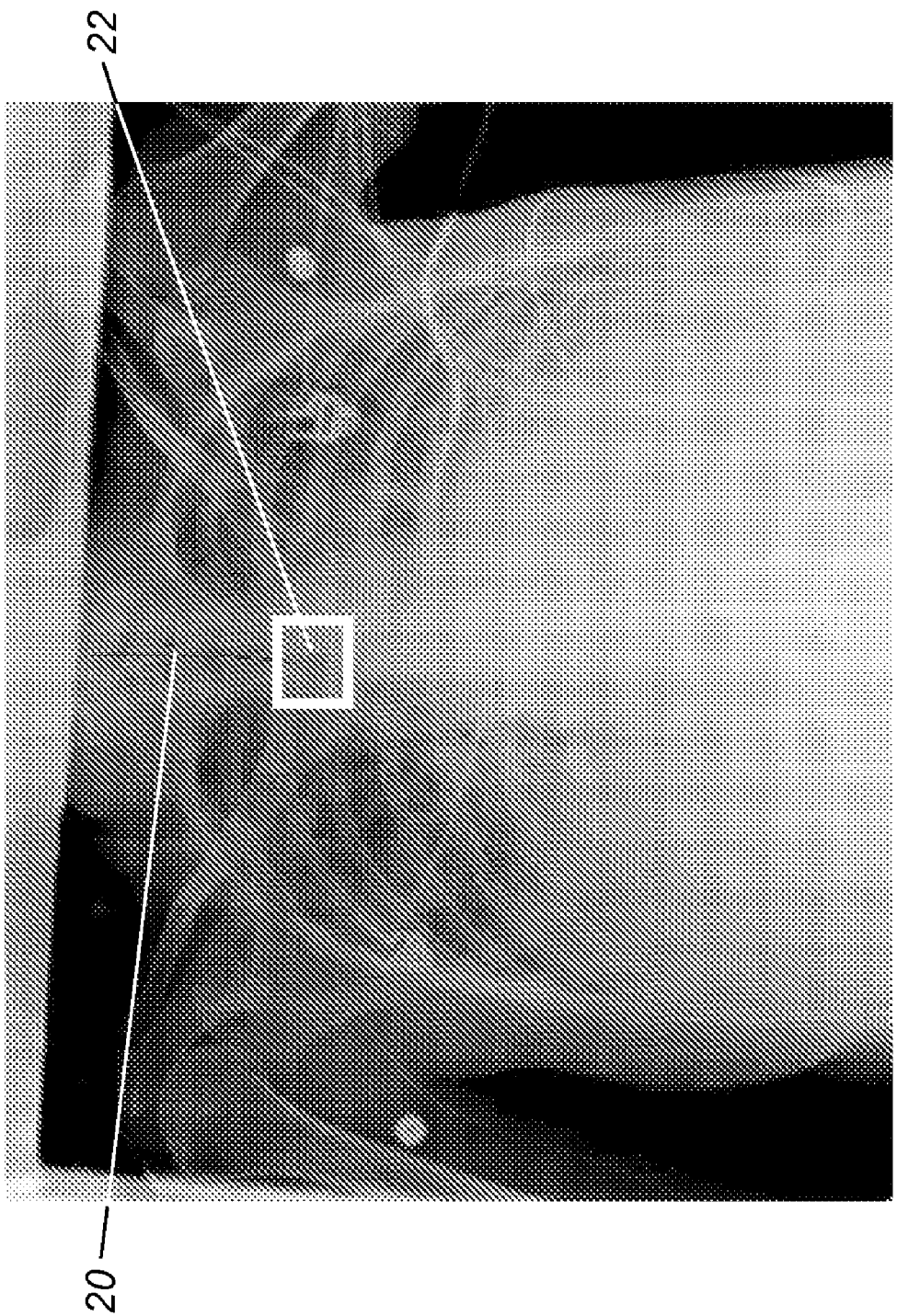
FIG. 2 is an example image for a chest x-ray showing ET tube position.

FIG. 2 shows one example image in which an ET tube 20 is detected. With this type of tube, the clinician desires to identify the location of the tip 22 and to determine whether tip 22 is appropriately positioned within the patient's body. In order to do this, it is advantageous to focus attention on a smaller area for further analysis. To do this once tip 22 is detected, ROI definition step 120 (FIG. 1) applies known techniques to define a reduced-size area of the image that is used for further image processing and assessment procedures. In one embodiment, the ROI is defined as that portion of the image within specific vertical and horizontal dimensions of the detected tip. More complex metrics can be used, based on patient size as obtained from the image dimensions, for example.

Figure 3:
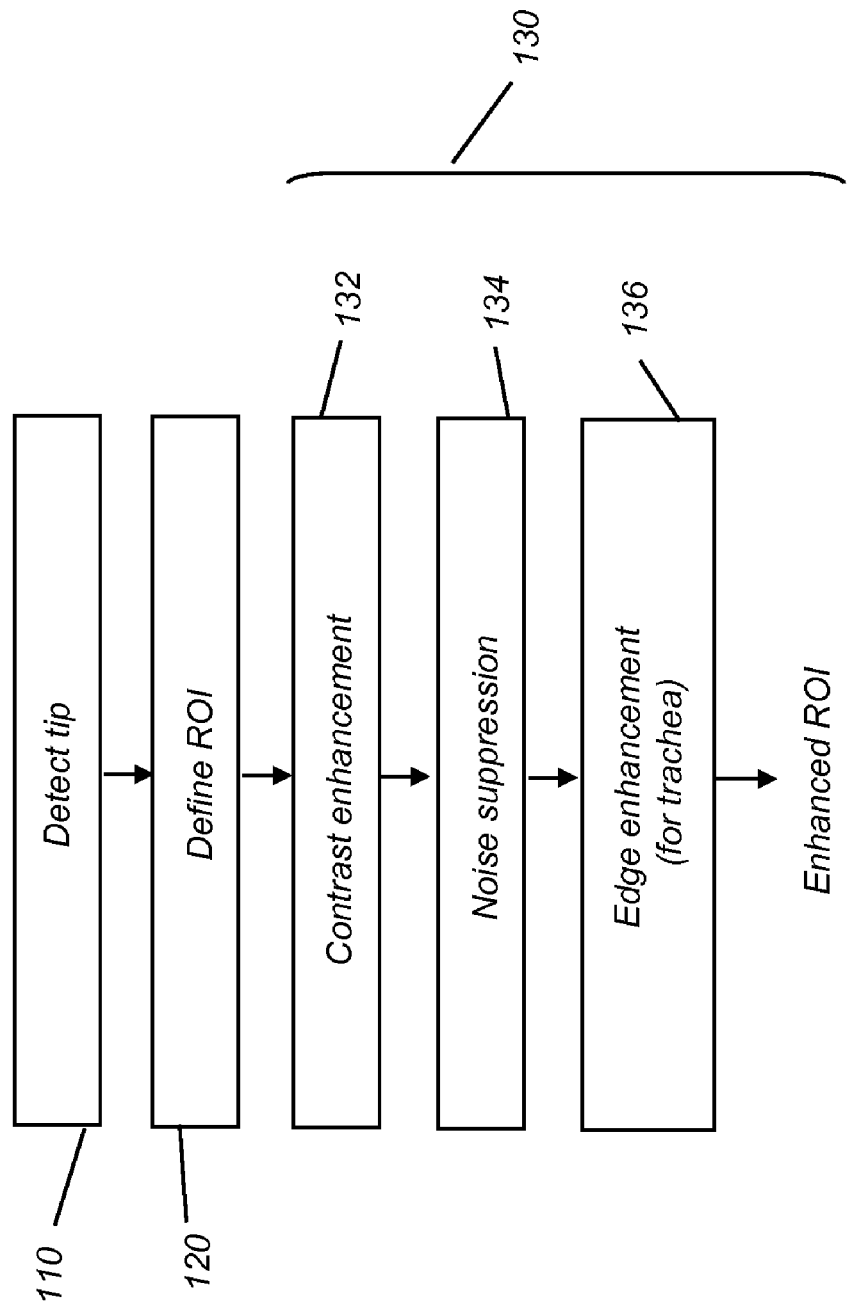
FIG. 3 is a logic flow diagram for steps that expand upon enhancement of a Region of Interest (ROI) in one embodiment.

One sequence for ROI enhancement step 130 is shown in the expanded logic flow diagram of FIG. 3. Following tip detection step 110 and ROI definition step 120, a contrast enhancement step 132 is executed. Techniques familiar to those skilled in the image processing arts, such as background trend correction or other processing, may be used for enhancing contrast in step 132, enhancing anatomical features within the ROI, adjusting the tone scale as necessary to bring it within a suitable range in order to obtain clearer definition of tip position. For the ET tube image, for example, both tone scale correction for the ROI and trachea edge detection within the ROI may be executed.

An optional noise suppression step 134 can then be executed. In noise suppression step 134, known anisotropic noise correction or other suppression techniques may be used to reduce the relative level of noise within the ROI image.

Following noise suppression step 134, an edge enhancement step 136 is performed. This step uses various known edge detection and enhancement techniques in order to more clearly define the anatomical structure that has high relevance to tip position. An enhanced ROI is thus produced, as shown at the end of the process steps in FIG. 3. As was described with reference to FIG. 1, the enhanced ROI can then be provided for display in display output step 140.

Figure 4A:
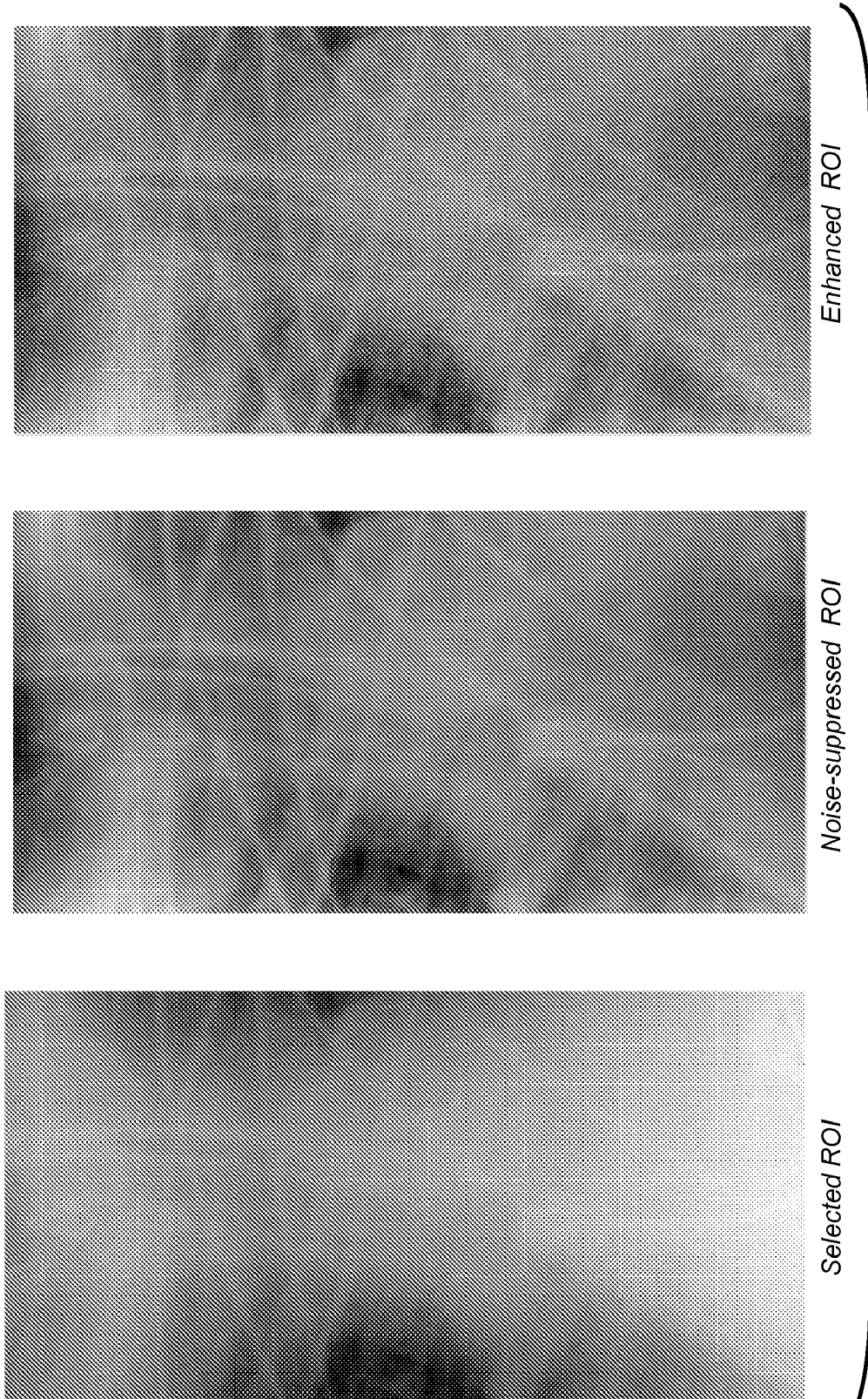
FIGS. 4A and 4B are ROI views for ET tube tip detection at different stages of processing.
Figure 4B:
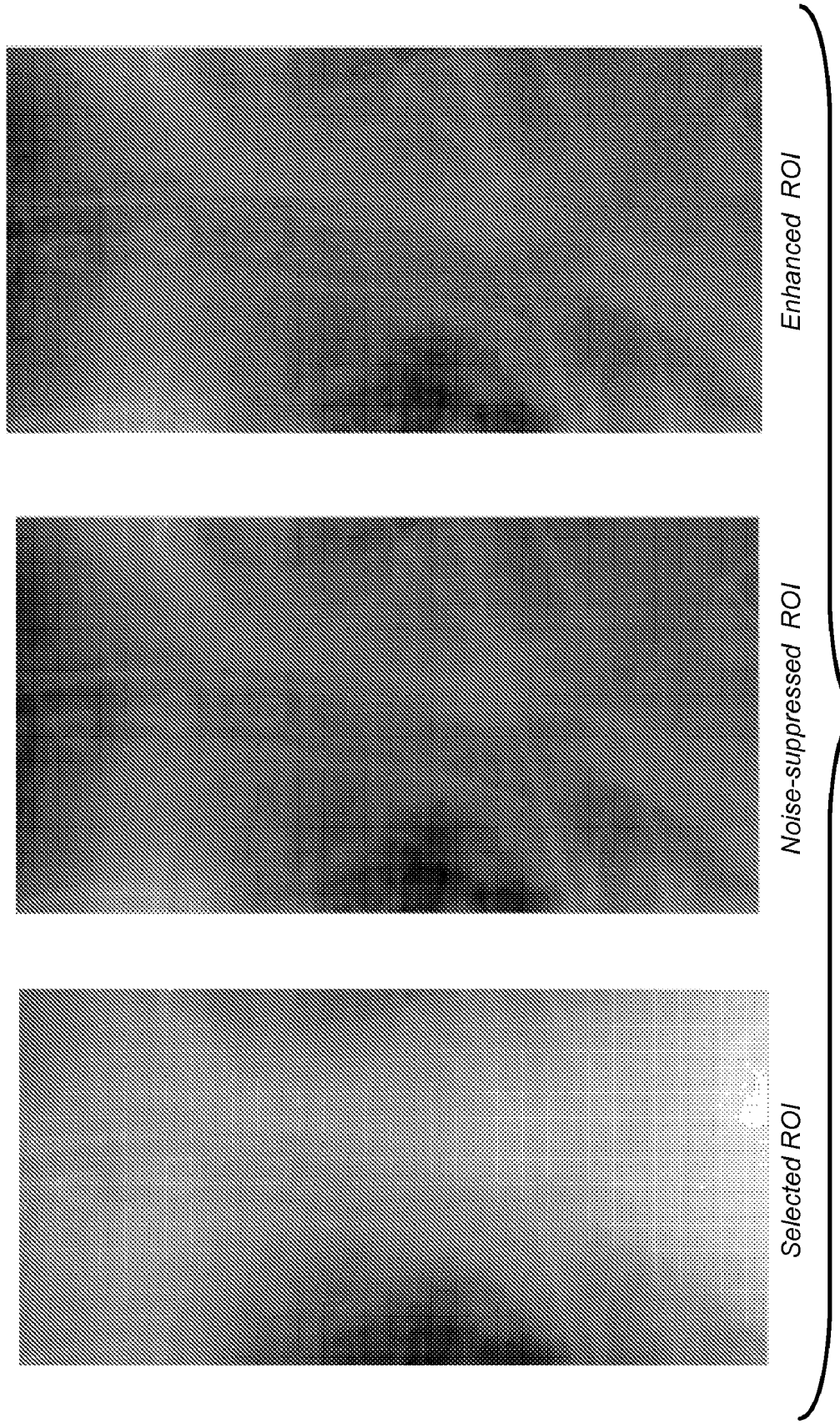

FIGS. 4A and 4B show example images at different stages of processing for ET detection. From left to right, each of these figures shows the succession of images from the selected ROI obtained in ROI definition step 120 to the noise-suppressed ROI provided from noise suppression step 134 to the enhanced ROI obtained in step 130.

Figure 5:
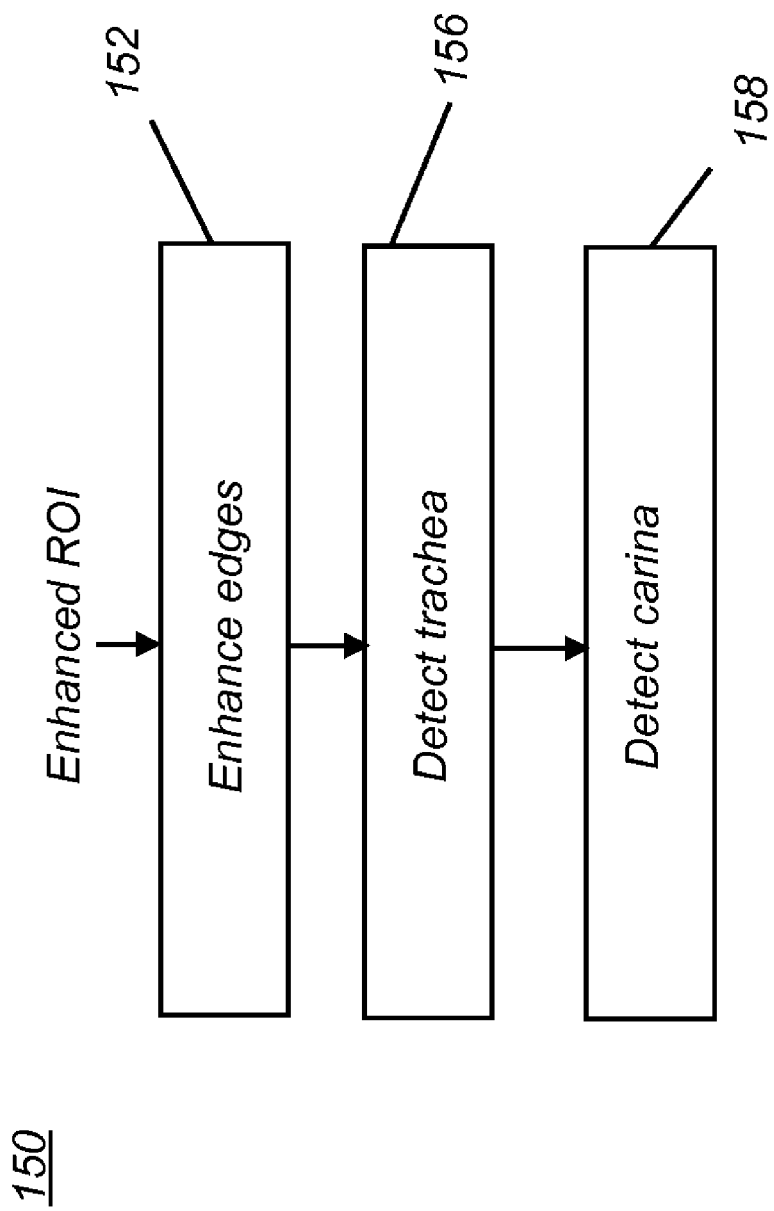
FIG. 5 is a logic flow diagram showing steps for detection of surrounding critical anatomy within an ROI in one embodiment.

The logic flow diagram of FIG. 5 expands upon anatomy detection step 150, shown as part of the overall process in FIG. 1. Anatomy detection step 150 takes the enhanced ROI provided as output from ROI enhancement step 130 (FIGS. 1 and 3) and executes procedures that identify specific anatomy that is relevant for the type of tubing that is of interest. Using the example ET tube placement shown in FIG. 6, the description that follows shows the sequence of processes that are used for detection of a trachea 60 and a carina 50 in anatomy detection step 150. An optional edge enhancement step 152 performs edge enhancement for the anatomical structure of interest. For the ET tube example used herein, edge enhancement can be used to provide improved definition of the trachea. A critical area detection step 156 then detects an important anatomical feature or landmark that can be used as a reference for the last step shown in FIG. 5, a critical structure detection step 158. For the ET example given, critical area detection step 156 detects that portion of the trachea lying within the ROI. Critical structure detection step 158 detects the carina.

Trachea Detection

Figure 7:
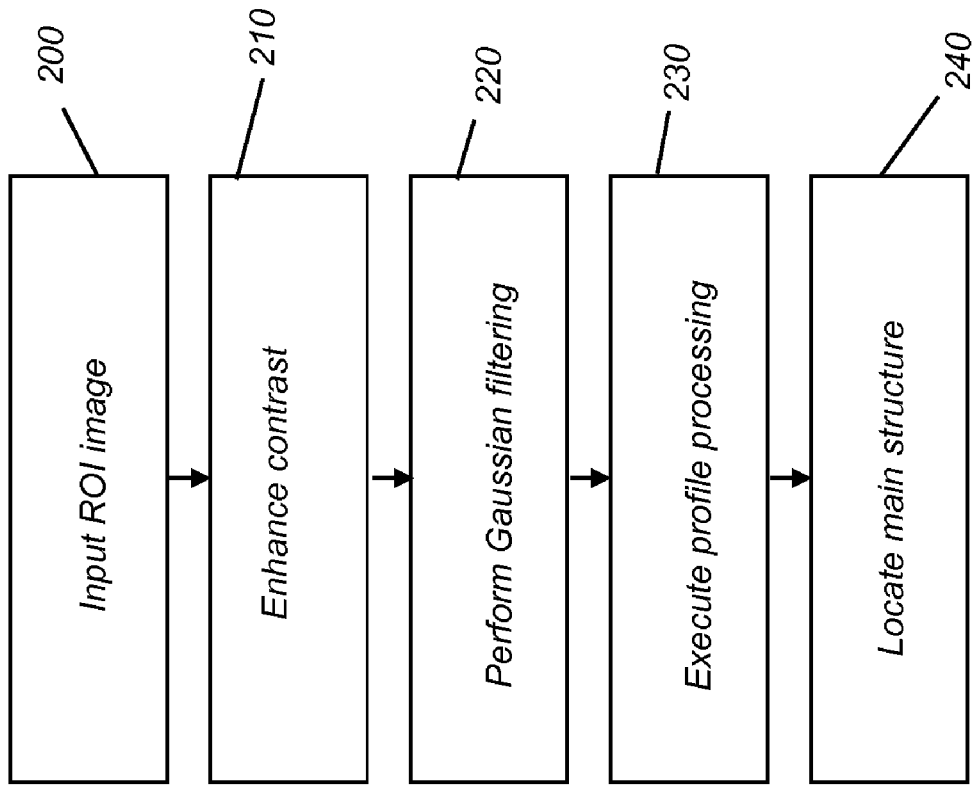
FIG. 7 is a logic flow diagram showing a sequence for locating the main structure of the trachea in one embodiment.
Figure 8C:
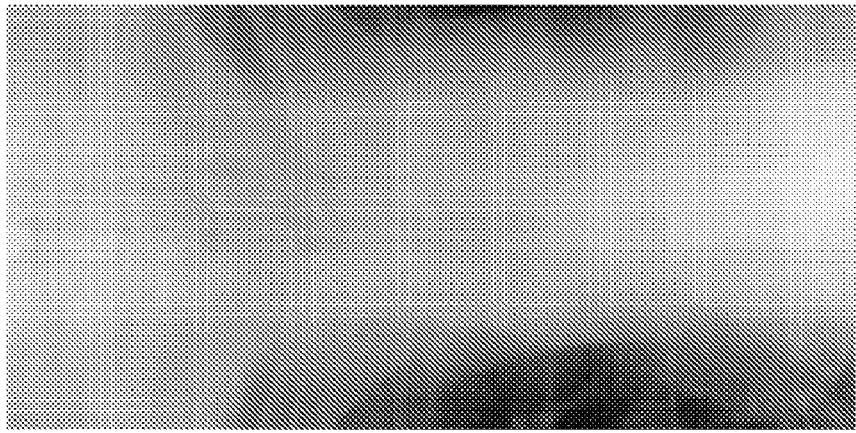
FIGS. 8A, 8B, and 8C show stages in a process for identifying main structure using the sequence given in FIG. 7.
Figure 8B:
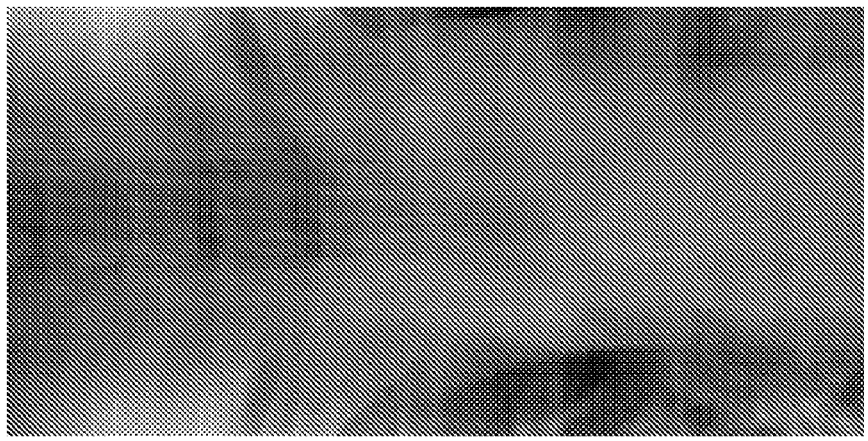
Figure 8A:
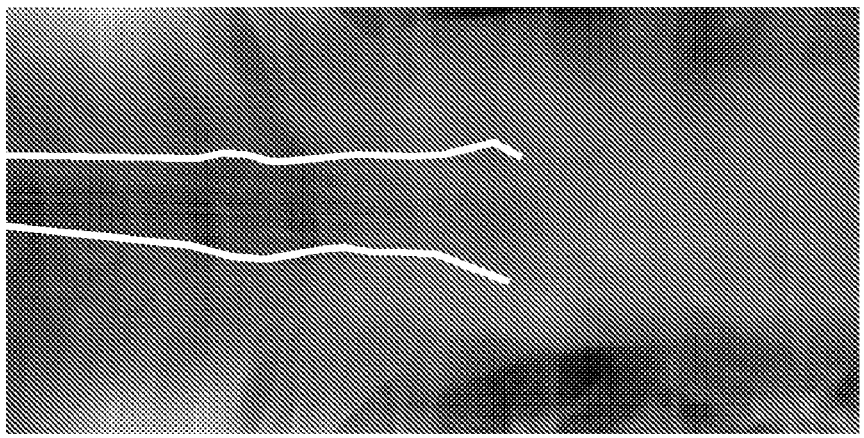

The logic flow diagram of FIG. 7 shows a sequence of steps for trachea detection in one embodiment. In an ROI input step 200, the ROI is identified as an area of the image centered at the tip of the tube. A standard-sized rectangular area of 1024× 512 pixels is used. FIG. 8A shows an ROI by way of example. A contrast enhancement step 210 follows. For this step, known background trend correction or other contrast enhancement method can be used, compensating for noise and background content in order to improve contrast. FIG. 8B shows the ROI of FIG. 8A after contrast enhancement has been performed. An optional filtering step 220 can then be executed, applying a Gaussian filter or other filter type in order to reduce image noise effects. This step helps to smooth the data profile and prepares the image data for image analysis tools. A profile processing step 230 provides gray-scale profiling of the image in order to detect the type of pixel transitions that indicate tubing and other structures. Completion of profile processing step 230 then enables the edges of the trachea to be traced, as is shown in FIG. 8C.

Figure 9:
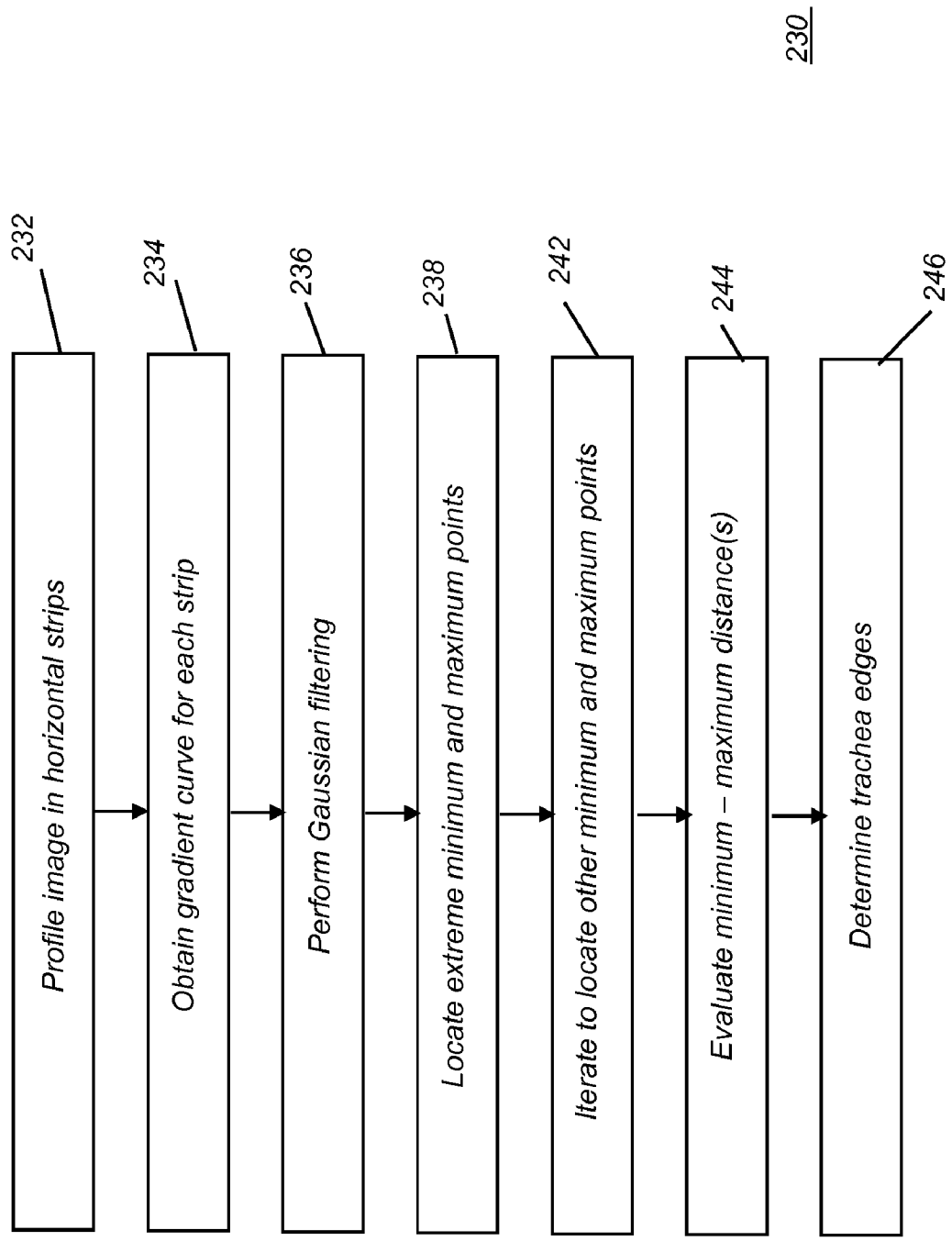
FIG. 9 is a logic flow diagram that shows a sequence for detecting trachea edges in one embodiment.

The logic flow diagram of FIG. 9 shows a sequence of steps for profile processing, such as can be used for profile processing step 230 in the sequence of FIG. 8. In a profiling step 232, a grayscale profile is obtained by taking a horizontal "slice" or section through the ROI image of some number of rows of pixels in width, such as 20 rows wide. This obtains the average value for each pixel position and enables a profile that can be used for identifying the trachea to be obtained.

Figure 10:
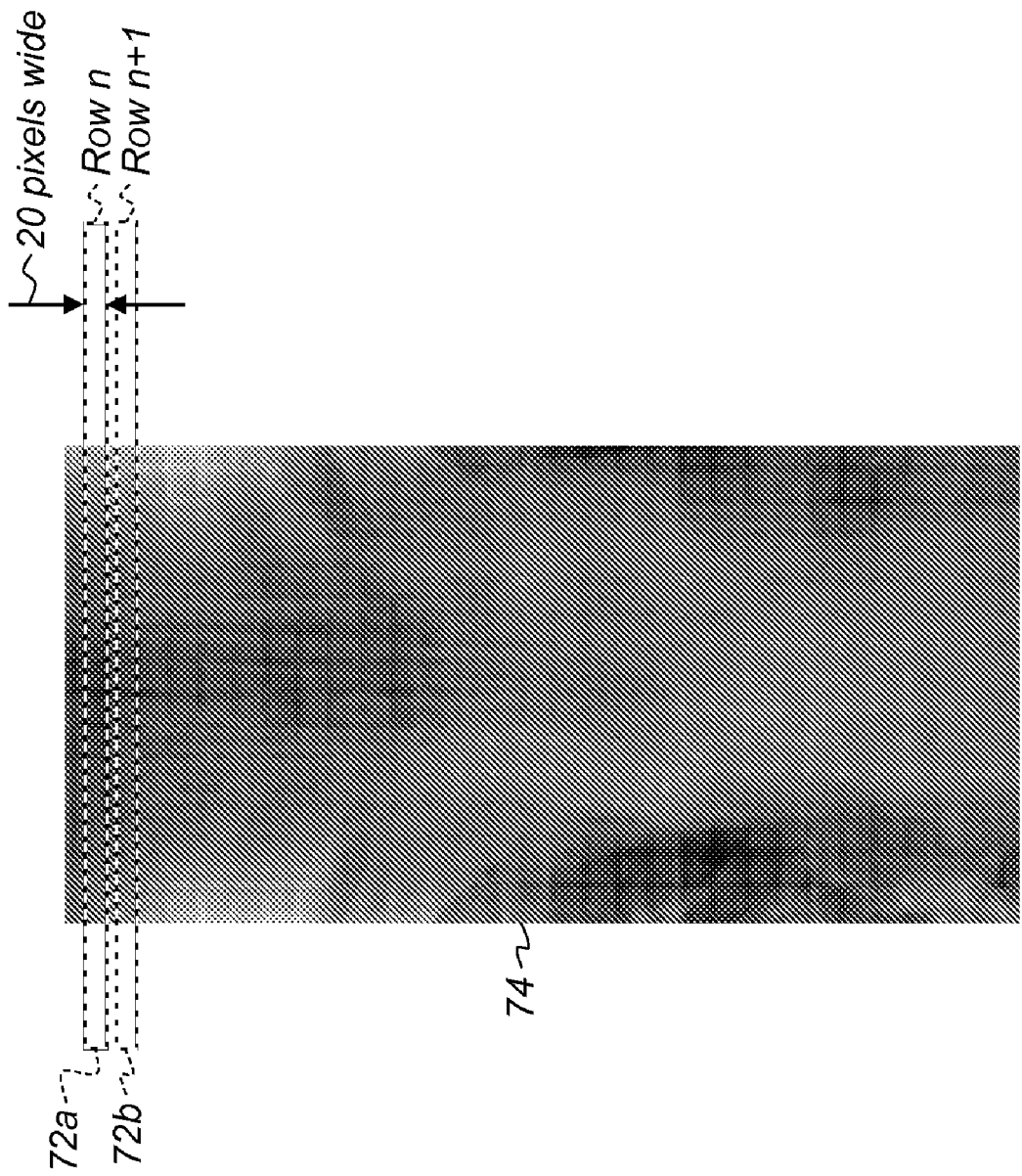
FIG. 10 shows an ROI that is row-processed in order to obtain profile data.

FIG. 10 shows how profiling step 232 is executed for profiling an ROI 74 for trachea detection in one embodiment. The graphs of FIG. 11A then show the smoothed grayscale profiles 172a, 172b for two adjacent horizontally extended sections 72a and 72b of the ROI of FIG. 10. FIG. 11B shows the corresponding smoothed gradient curves 174a and 174b for each of the adjacent horizontally extended sections 72a and 72b. Beginning with FIG. 10, two sections 72a and 72b are profiled. Each section 72a, 72b averages some number of rows of pixels in the ROI image itself.

Figure 11A:
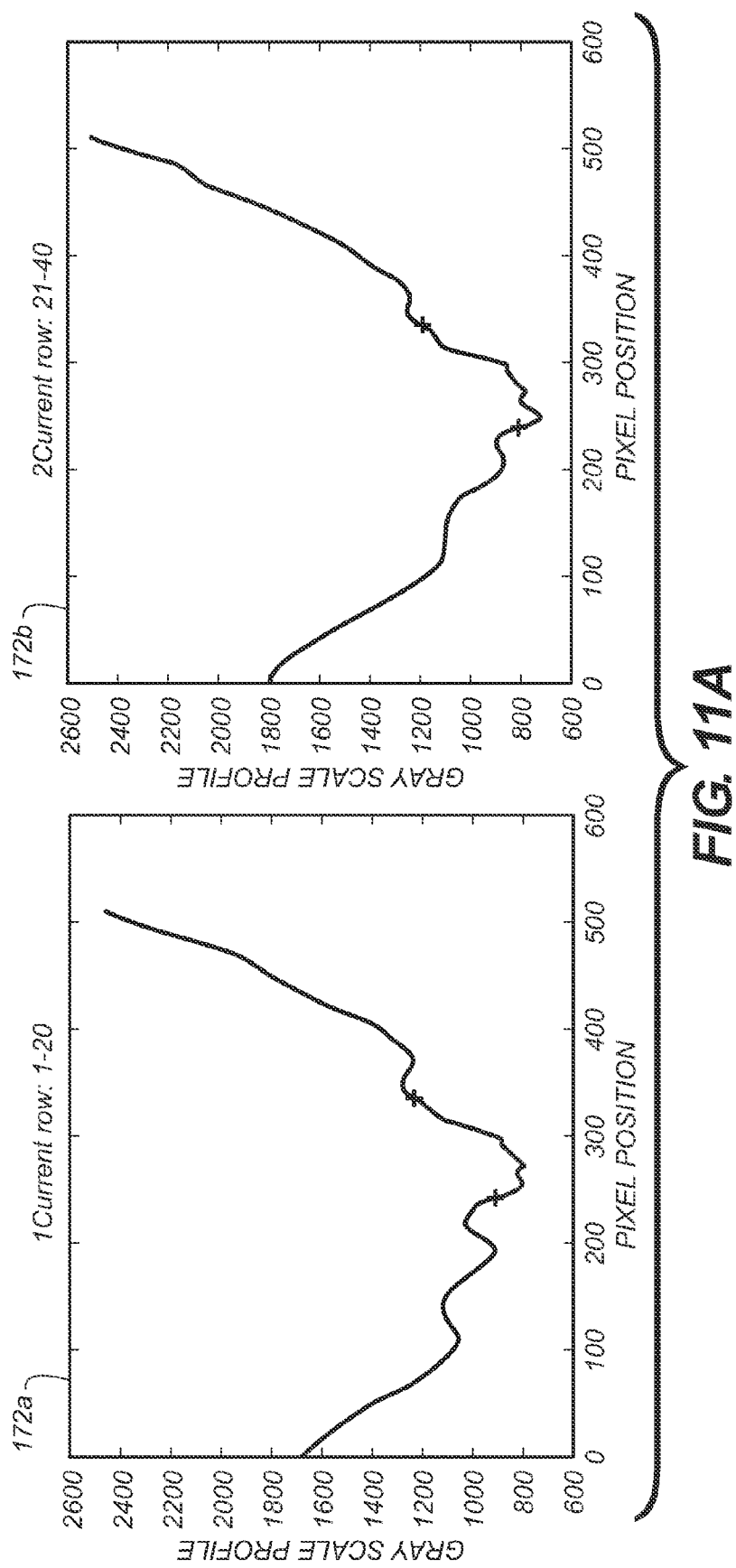
FIG. 11A shows gray scale profiles obtained for the rows shown in FIG. 10.
Figure 11B:
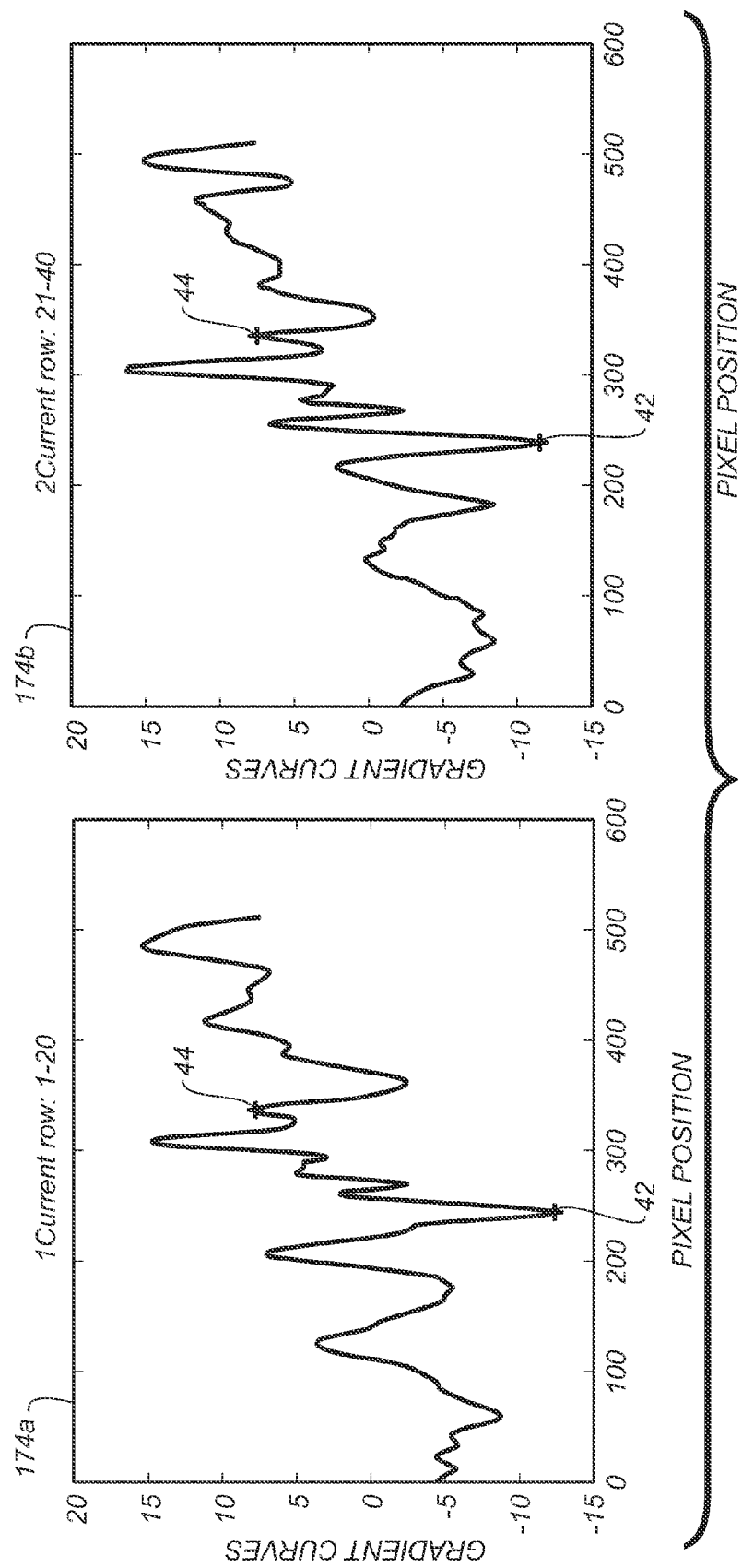
FIG. 11B shows gradient curves calculated for the profiles of FIG. 11A.

For the profile and gradient graphs in FIGS. 11A and 11B, the x-axis indicates the column position of the ROI image. In this example, the FIG. 10 ROI has 512 columns. The y-axis in FIG. 11A gives the mean grayscale value for the multiple averaged pixels in that portion of the pixel column that corresponds to the x position for that section. In one embodiment, where ROI 72 has 512×1024 pixels, there are 51 grayscale profile curves generated for the ROI (each corresponding to a 20-row section of pixels as shown in FIG. 10). In terms of FIG. 11A, this means that there are 51 graphs showing profile data.

Still describing the process steps of FIG. 9, a gradient curve generation step 234 generates the gradient curve for each of the grayscale profile curves, such as the gradient curves 174a and 174b shown in FIG. 11B. A filtering step 236 then applies a Gaussian filter to reduce noise effects for smoothing the gradient profiles.

The next sequence of steps in FIG. 9 can be more easily understood by considering what the grayscale profiles and gradient curves of FIGS. 11A and 11B show. Edge points on the gradient curve are shown by local minimum or maximum values, indicating a rapid pixel tone transition from bright to dark or dark to bright. A transition detection step 238 and an iteration step 242 are used to detect edge points by analysis of gradient curves in this way, working inward toward trachea edge values that are generally centered about the ROI. Referring to FIG. 11B, for example, it can be seen that points 42 and 44 represent edge values that are likely to correspond to trachea edges. Other maximum and minimum values can also be identified as shown by iteration step 242, helping to reduce the likelihood of false positives. Determining which points are most likely requires knowledge of patient size and trachea width, known beforehand, and depends on making some likely assumptions on trachea centering within the ROI. An evaluation step 244 applies some measurement criteria and, possibly, trained system logic to the problem of trachea identification. Among possible measurement criteria are variables such as horizontal displacement of an edge from the edge of the ET tube or other tube. An edge determination step 246 can then be used to trace and display trachea edges as was shown earlier with reference to FIG. 8C.

Carina Detection

Detection of the trachea branching point or carina 50 is needed for determining the actual position of the tip of the ET tube relative to the patient anatomy. Determining the distance between the tip of the ET tube and the carina allows program logic to warn the user when ET tip placement may be incorrect or is even hazardous. The carina location provides a more accurate reference point than is available with other detectable anatomy features.

Figure 12:
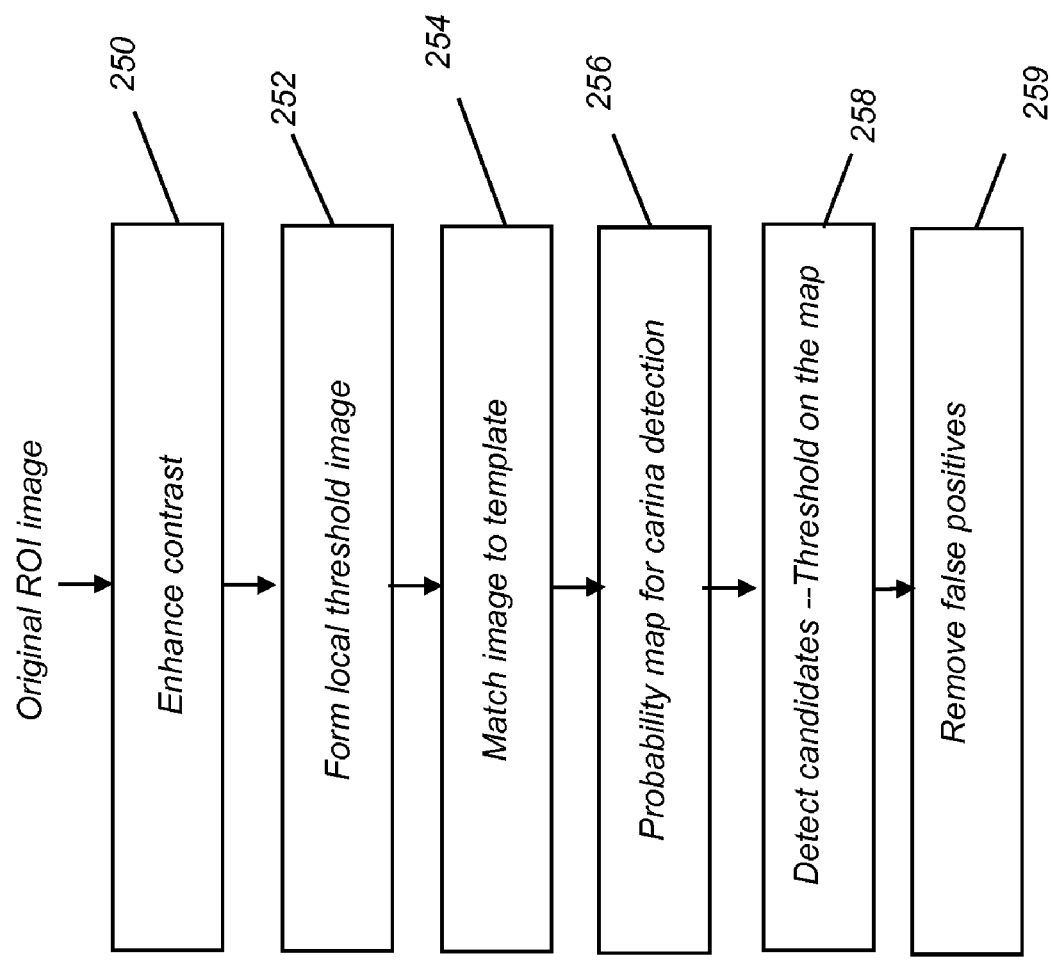
FIG. 12 is a logic flow diagram that shows detection of the carina in one embodiment.
Figure 13:
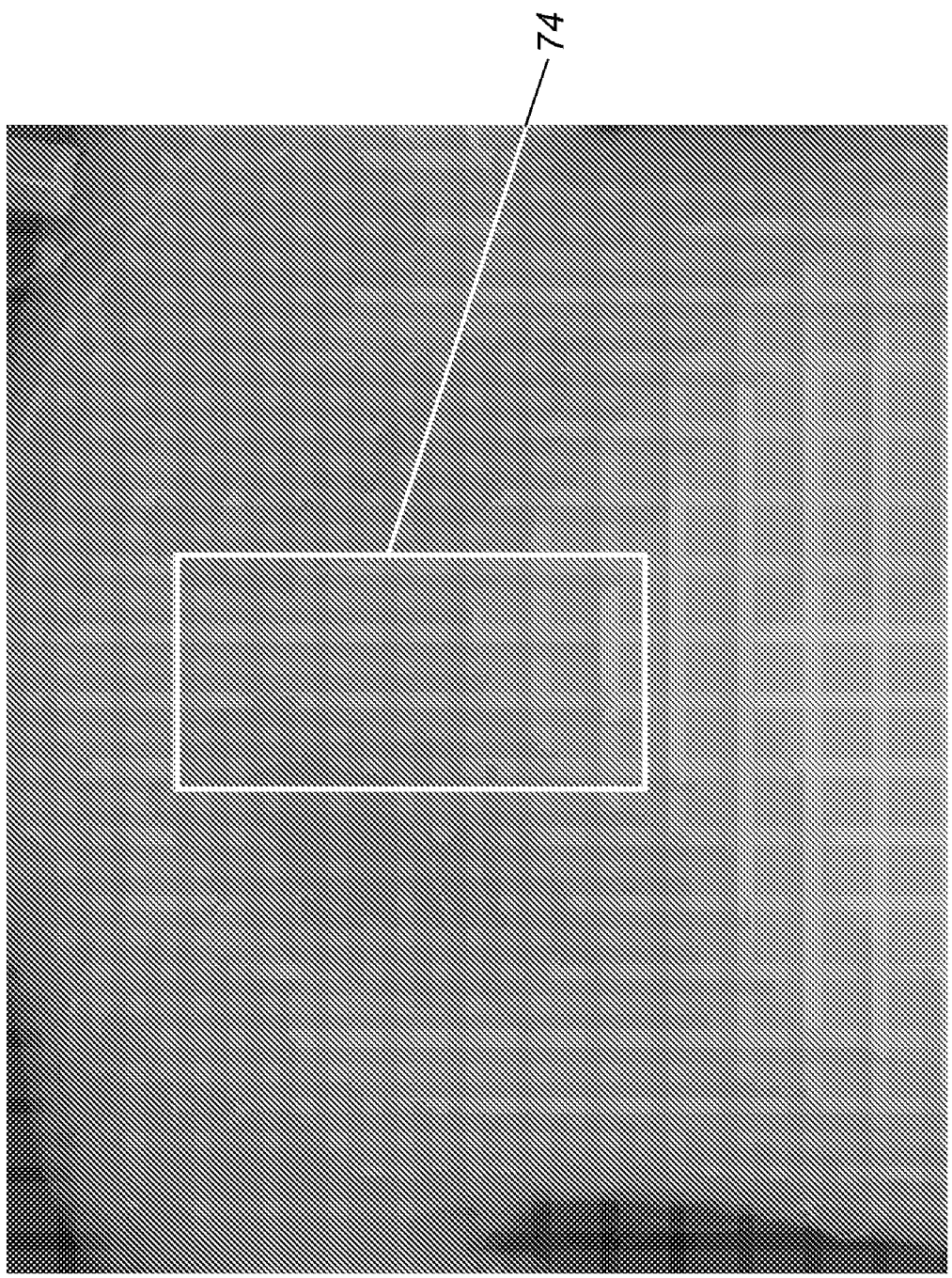
FIG. 13 shows an ROI obtained from a radiological image.
Figure 14B:
Figure 14A:
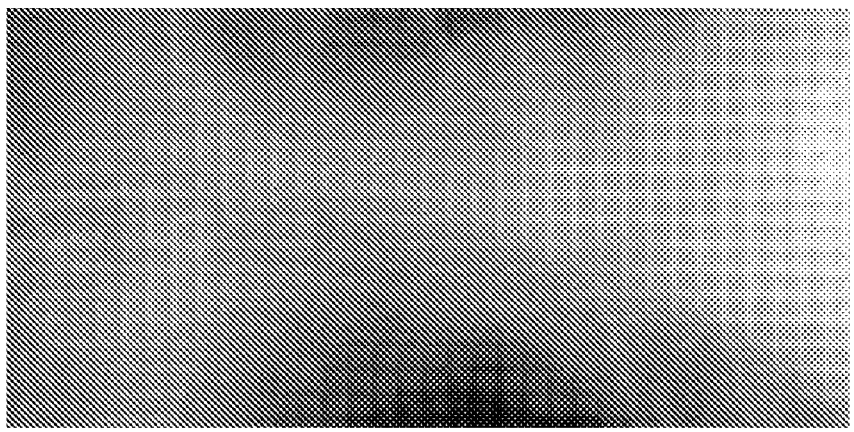

The logic flow diagram of FIG. 12 shows a sequence of steps for carina detection in one embodiment. FIGS. 13 and 14A-14E show the appearance of some exemplary images for each step. FIG. 14A shows the original image of ROI 74. The original ROI image 74, obtained from the full image as shown in FIG. 13, is first processed using a contrast enhancement step 250. FIG. 14B shows the ROI image after contrast enhancement. Enhancement methods, such as background trend correction, are known in the art.

Figure 14D:
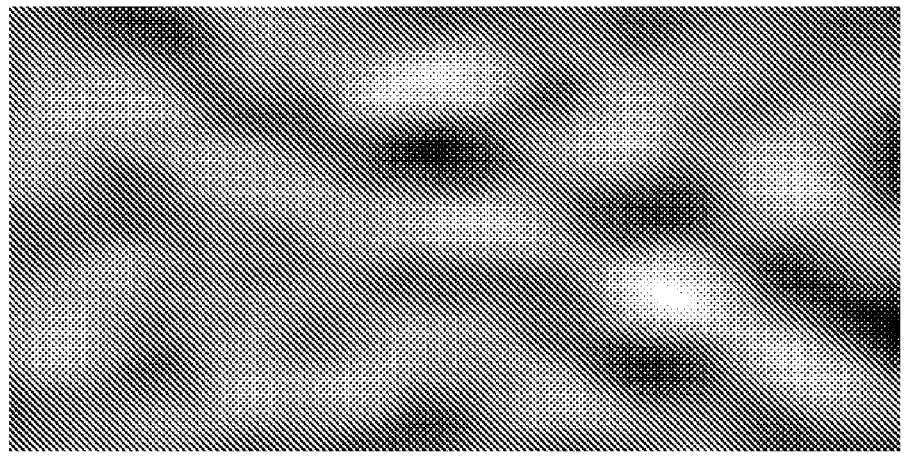
Figure 14C:

A threshold imaging step 252 then forms a local threshold image that is used in subsequent processing. FIG. 14C shows one example of a threshold image that has been formed for carina detection. This image appears as a binary image, with either light or dark pixels, but with no intermediate tones. In conventional thresholding procedure, a global threshold value is used to determine which pixels are light, which are dark. Each pixel in the image is compared with this global threshold and the corresponding result set to a light or dark value based on this comparison. In one embodiment of the present invention, an adaptive local threshold value is used, rather than a global threshold value. To do this, the mean intensity value of an adjacent pixel is used, with a sequence of steps such as the following:

for each point (x,y) in the ROI(x,y), calculate

T=average value of a kernel [50×50] centered at x,y

If ROI(x,y)>T, ROI(x,y)=0

If ROI(x,y)<=T, ROI(x,y)=1 where threshold T is determined from multiple pixel values. A 50×50 template is used in this sequence.

A template-matching image is then matched to the binary threshold image that is obtained in a template matching step 254 (FIG. 12). FIG. 15 shows a template 78 used as a kernel for carina detection in this process. In one embodiment, this template is 50×50 pixels; however, the scale of this template can be varied to suit the imaging resolution and modality. Each pixel in the binary threshold image of FIG. 14C is processed using a correlation mapping with an appropriate kernel (such as that in FIG. 15). A correlation mapping such as the following can be used:

$$\text{Map}(x, y) = 1/N \sum_{i,j=-a}^{i,j=a} ROI(x+i, y+j) * \text{Kernel}(x+i, y+j)$$

where a is an appropriate kernel size and N is a predefined scaling factor. FIG. 14D shows a template-matching or probability image Map (x,y) that is obtained as the result of this process. The brightness of each point in Map (x,y) corresponds to the probability that the corresponding image point is at the carina. As a cursory examination of FIG. 14D shows, there are a few possible candidate areas indicated by brighter regions in this mapping.

A probability map for carina detection is then used in a probability map test 256. A candidate detection step 258 identifies likely candidates for carina location by applying a predetermined threshold to the probability map. For example, the threshold may be selected to be 90% of maximum value for a given probability map. Depending on the user preference on detection sensitivity or tolerance on false-positive detections, the threshold can be set lower or higher. Further, the threshold level can be set differently for each image, for example, based on the limit allowed on the maximum numbers of the total detections for each image. One or more candidates can be detected at step 258. FIG. 14E shows a possible carina position for this ROI, based on the processing described with reference to FIG. 12.

Figure 16:
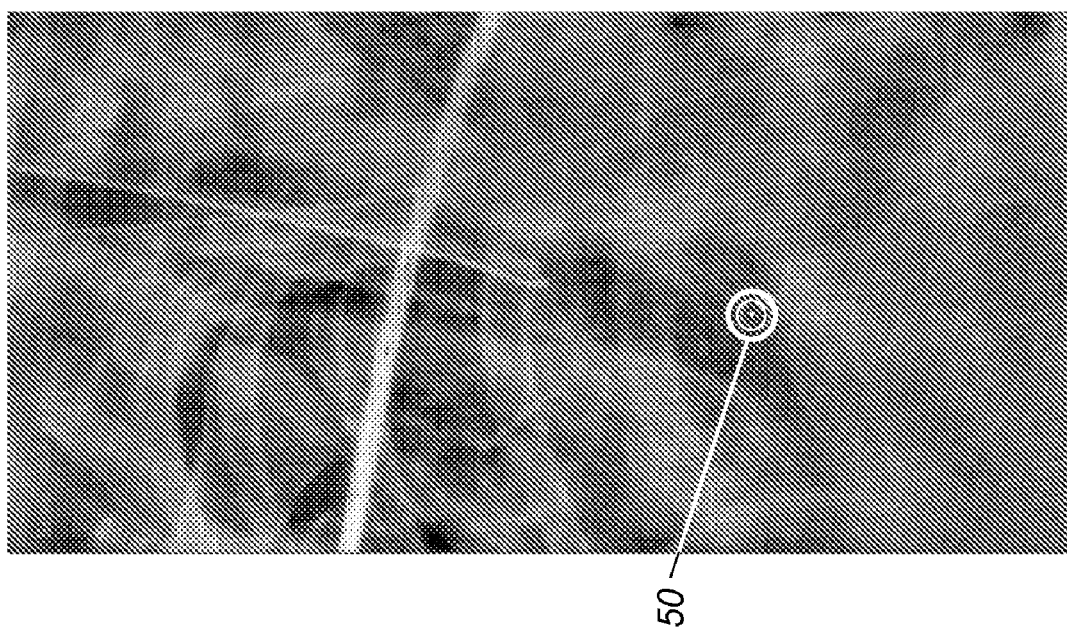
FIG. 16 shows an ROI prior to carina detection.
Figure 17:
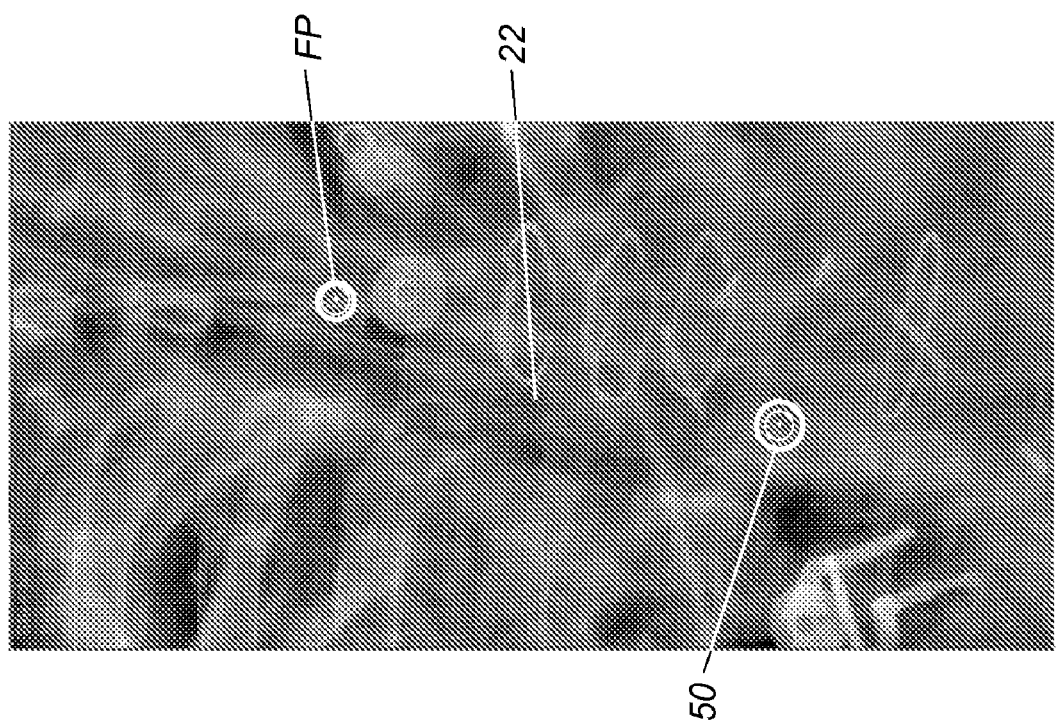
FIG. 17 shows the ROI with true and false positive detections.

More than one position may be identified by this process, yielding a number of false positives. Removal of false positives, shown at a step 259 in FIG. 12, is a follow-up to the processing steps of FIG. 12. FIG. 16 shows a correctly identified carina 50 using this processing. FIG. 17 shows an image with one false positive (FP), one true positive at carina 50, and showing the ET tube tip 22. The criteria used for removing false-positive detections may be based on the geometric location relative to the locations of the detected trachea and tube. If the detected points are located outside of the trachea, these detected points will be removed as false-positive detections. If the detected points are located within the main trachea as detected in FIG. 8c, the detected points will be removed as false-positive detections.

In images where the trachea or carina is not visible, landmark structures such as the clavicle and cervical vertebrates (C1-C7) can be detected to determine whether or not the tip is appropriately positioned.

Classifying Mal-positioning Probability

Figure 6:
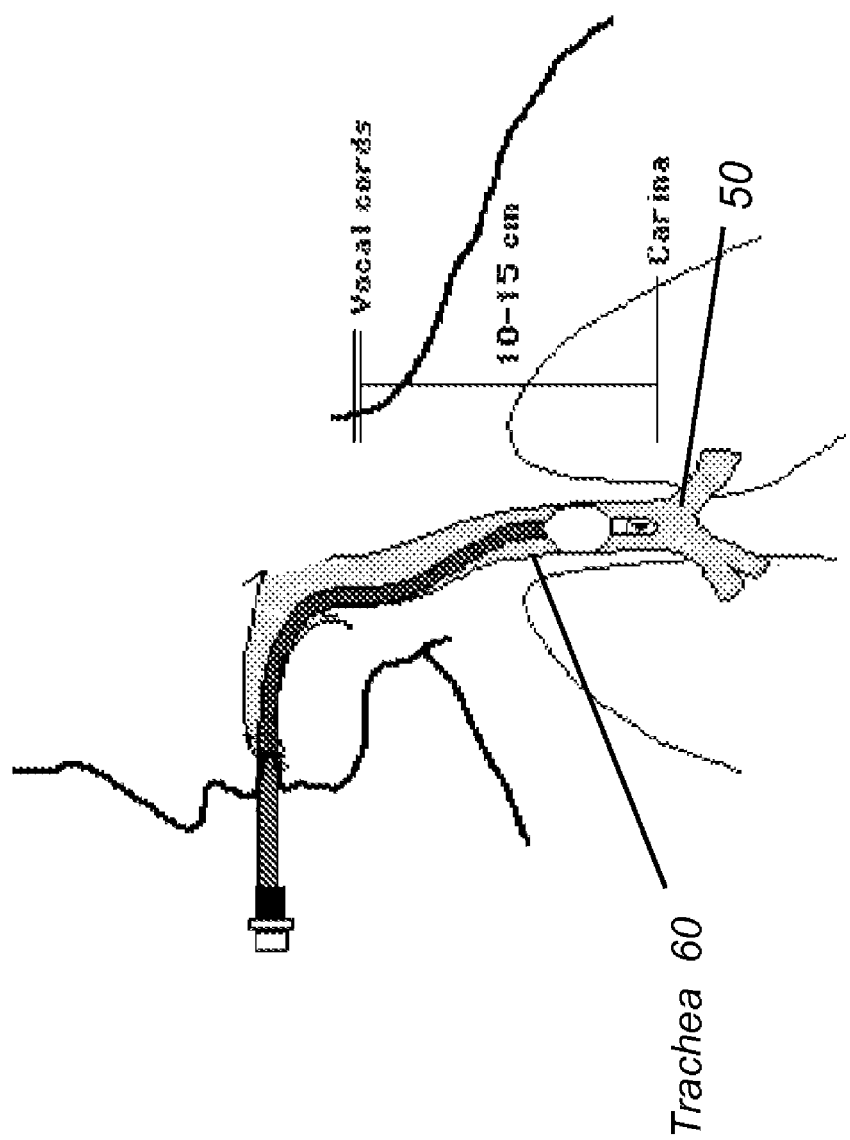
FIG. 6 is a schematic diagram showing ET tube placement relative to surrounding anatomy.

As noted earlier, the ideal position of the ET tube in the adult human patient is about 3-4 cm above the carina. In an average adult, this typically places the distal tip of the tube appropriately midway between the vocal cords and the carina (FIG. 6).

Referring back to the logic flow diagram of FIG. 1, relative positioning determination step 160 uses the information that has been obtained from tip detection for the specific type of tubing that is of interest and uses trachea and carina detection, such as the methods just described. A relative distance is calculated for step 160. Then, in steps 170 and 180, a mal-positioning probability and, optionally, a mal-positioning classification are obtained.

Figure 18:
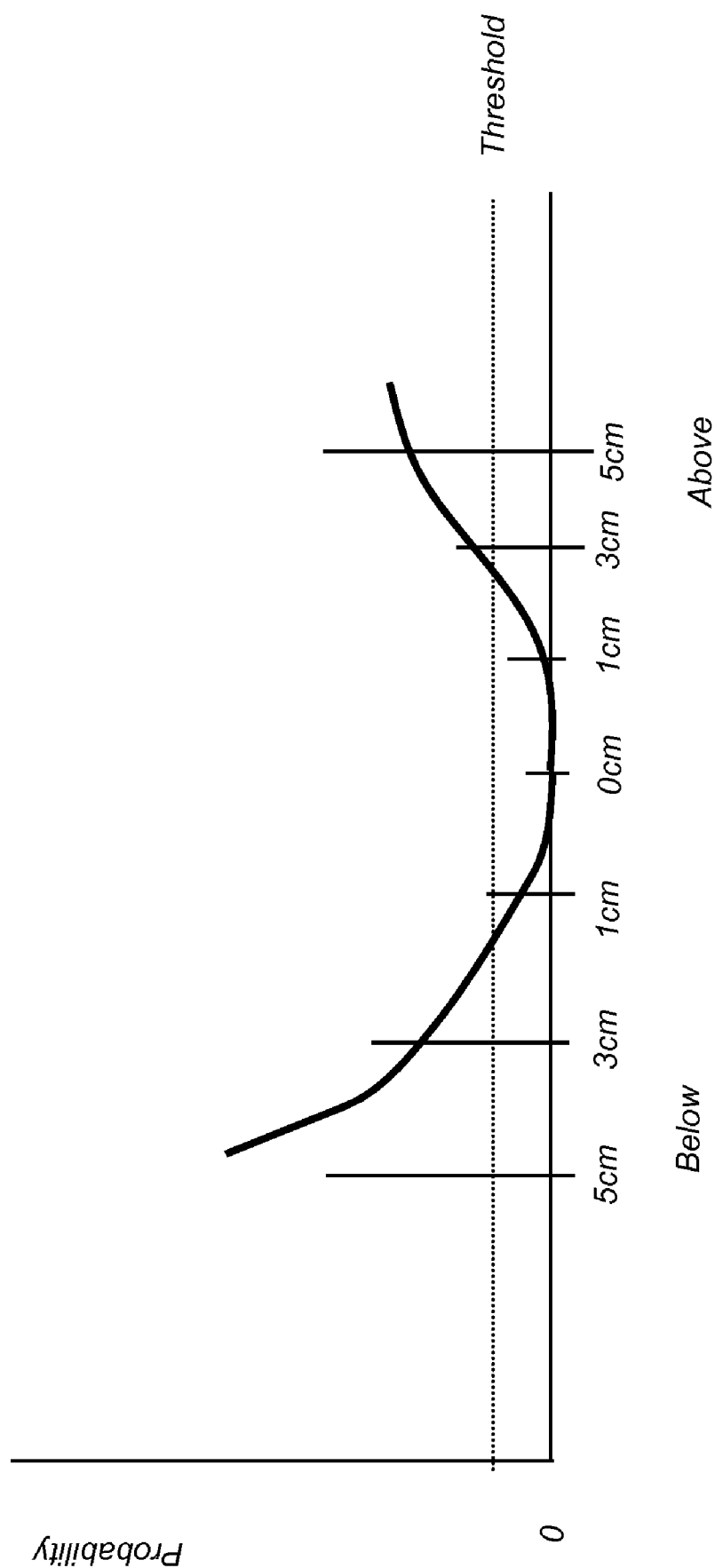
FIG. 18 shows a probability curve for mal-positioning.

The graph of FIG. 18 shows how probability can be computed based on the results of relative distance calculation in step 160. As the curve shows, probability of mal-positioning increases with increased distance above and below a reference point, shown as 0 cm, that represents an ideal distance above the carina. A threshold can be applied to the probability to make a binary decision for appropriate or mal-positioned tube. The threshold level and curve shape may be adjustable in various embodiments.

Classification in step 180 (FIG. 1) can be based on a number of factors, including relative risk for the patient and relative effectiveness of tube use with the tip at the detected position. Rules on selected features, such as distances from the detected carina and position relative to the detected main trachea can be used to provide at least some measure of classification. For example, in a particular patient image, the tip of an ET tube may be located within a range of positions from below the carina to above the carina. Classification may be expressed as a numeric value or with a text string, for example that can be displayed or otherwise reported to an operator. Classification can be a score, as a value given within a numeric range that indicates relative positioning accuracy. Alternately, classification can be binary, with a first value representing acceptable positioning and a second value representing positioning that is not acceptable.

Mal-positioning Reporting

Figure 19:
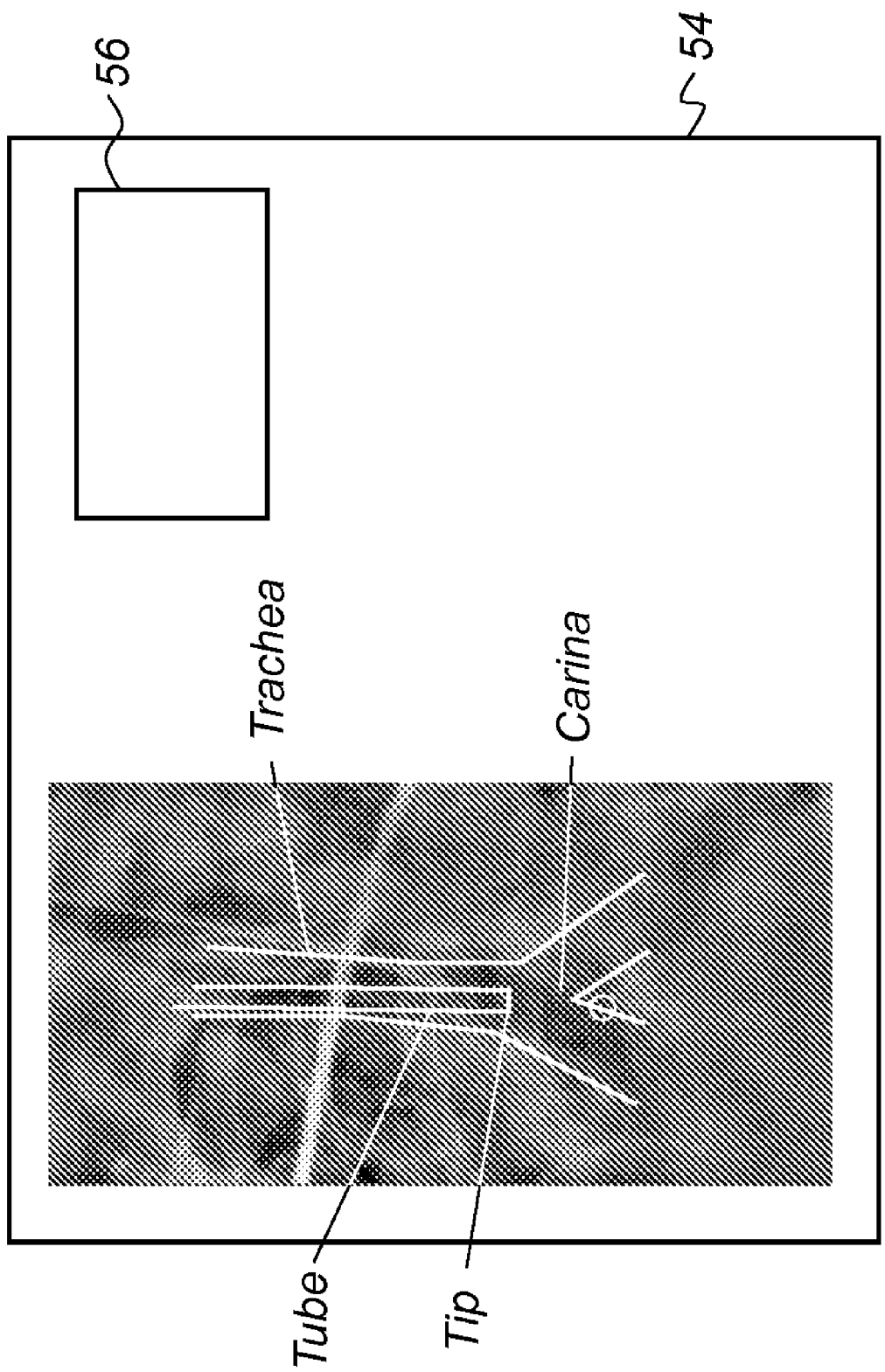
FIG. 19 shows a display on a display monitor for reporting mal-positioning.

One benefit of the method of the present invention relates to the capability for enhanced display and reporting of tube and tip position. Referring to FIG. 19, there is shown a highlighted image that appears on a display 54 that serves as a control monitor for ET tube positioning in one embodiment. A message area 56 can be used to display a warning message or classification result, such as a probability value or classification level, that reports likely mal-positioning to the operator. Other positioning data can also be reported to the operator, including calculated dimension values or other variables.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, as noted earlier, any of a number of different methods could be used for contrast enhancement, including background trend correction and foreign object suppression, for detecting the trachea and carina and other anatomical structures, and for detecting edges of the tube and tip. Also, the methods of the invention may be used to detect other types of medical devices or other foreign objects that have been inserted into the body and require proper positioning, such as pacemakers, balloon catheters and stents. Similarly, the methods of the invention maybe used in emergency care to accurately determine the positions within the body of invasive foreign objects such as bullets or knives.

Thus, what is provided is a method for enhancing a diagnostic image in order to detect the position of the tip of a tube that is positioned within the patient and to report a possible mal-positioning error.

PARTS LIST

20. Tube
22. Tip
42, 44. Point
50. Carina
54. Display
56. Message area
60. Trachea
72a, 72b. Section
74. Region of interest (ROI)
78. Template
100-180. Logic steps
172a, 172b. Grayscale profiles

174a, 174b. Gradient curves
200-259. Logic steps
FP. False positive

The invention claimed is:

1. A method for processing a radiographic image of a patient comprising:
   obtaining radiographic image data;
   detecting the position of inserted tubing in the obtained image and determining the tubing tip location;
   detecting at least one anatomy structure within the obtained image; and
   calculating the probability for tip mal-positioning by determining the position of the tip relative to the at least one anatomy structure.

2. The method of claim 1 further comprising reporting a result according to the calculated tip mal-positioning probability.

3. The method of claim 1 further comprising classifying tubing tip mal-positioning according to the position of the tip relative to the at least one anatomy structure.

4. The method of claim 3 further comprising reporting a result according to the classification of tubing tip mal-positioning.

5. The method of claim 4 wherein reporting the result comprises displaying a value or text string on a control monitor.

6. The method of claim 1 further comprising:
   defining a region of interest in the neighborhood of the tubing tip location;
   detecting the at least one anatomy structure within the region of interest; and
   displaying the region of interest and highlighting the detected tubing tip in the display of the region of interest.

7. The method of claim 1 wherein detecting at least one anatomy structure comprises detecting the trachea.

8. The method of claim 7 wherein detecting the trachea comprises obtaining a profile of pixel values taken along multiple rows of pixels within the obtained image.

9. The method of claim 8 further comprising computing one or more gradient curves for one or more of the profiles obtained.

10. The method of claim 9 further comprising searching local minimum and local maximum values on the gradient curves to identify corresponding left and right edges of the trachea, as viewed in the radiographic image.

11. The method of claim 1 wherein detecting at least one anatomy structure comprises detecting the carina.

12. The method of claim 11 wherein detecting the carina comprises obtaining a threshold image.

13. The method of claim 12 wherein detecting the carina comprises matching features in the threshold image to a template.

14. The method of claim 11 further comprising:
   defining a region of interest in the neighborhood of the tubing tip location;
   detecting the at least one anatomy structure within the region of interest;
   generating a probability map for the region of interest by using a mapping sequence that applies a template as a kernel;
   applying a threshold to the probability map to identify one or more candidate areas of the image; and
   removing false positive areas from the one or more candidate areas.

15. A method for processing a radiographic image of a patient comprising:
   obtaining radiographic image data;
   detecting the position of a foreign object within the body in the obtained image and determining the location of the object;
   detecting at least one anatomy structure within the obtained image; and
   calculating the probability for mal-positioning of the object by determining the position of the object relative to the at least one anatomy structure.

16. The method of claim 15 further comprising reporting a result according to the calculated mal-positioning probability.

17. The method of claim 16 wherein reporting the result comprises displaying a value or text string on a control monitor.

18. The method of claim 15 further comprising classifying mal-positioning according to the position of the object relative to the at least one anatomy structure.

19. The method of claim 18 further comprising reporting a result according to the classification of object mal-positioning.

20. The method of claim 15 further comprising:
   defining a region of interest in the neighborhood of the tubing tip location;
   detecting the at least one anatomy structure within the region of interest; and
   displaying the region of interest and highlighting the detected object in the display of the region of interest.

21. The method of claim 15 wherein detecting the at least one anatomy structure comprises obtaining a profile of pixel values taken along multiple rows of pixels within the obtained image.

22. The method of claim 21 further comprising computing one or more gradient curves for one or more of the profiles obtained.

23. The method of claim 22 further comprising searching local minimum and local maximum values on the gradient curves to identify corresponding edges of the anatomy structure as viewed in the radiographic image.

24. The method of claim 15 further comprising:
   generating a probability map for a region of interest by using a mapping sequence that applies a template as a kernel;
   applying a threshold to the probability map to identify one or more candidate areas of the image; and
   removing false positive areas from the one or more candidate areas.

* * * * *